(12) United States Patent
Dittmann

(10) Patent No.: US 7,610,915 B2
(45) Date of Patent: Nov. 3, 2009

(54) RESPIRATION SYSTEM

(75) Inventor: Ralf Dittmann, Blankensee (DE)

(73) Assignee: Dräger Medical AG & Co. KG, Lübeck (DE)

( * ) Notice: Subject to any disclaimer, the term of this patent is extended or adjusted under 35 U.S.C. 154(b) by 732 days.

(21) Appl. No.: 11/284,586

(22) Filed: Nov. 22, 2005

(65) Prior Publication Data

US 2006/0180150 A1 Aug. 17, 2006

(30) Foreign Application Priority Data

Feb. 17, 2005 (DE) ............ 10 2005 007 284

(51) Int. Cl.
*F16K 31/02* (2006.01)
*G06F 3/00* (2006.01)
(52) U.S. Cl. .............. 128/204.21; 128/204.18; 710/38
(58) Field of Classification Search ......... 128/200.24, 128/204.18, 204.21, 205.23, 203.12, 203.23, 128/203.27, 203.14, 203.16–203.17, 203.26; 600/300, 529, 532, 533, 538; 345/156, 157, 345/158; 710/38

See application file for complete search history.

(56) References Cited

U.S. PATENT DOCUMENTS

| | | | | |
|---|---|---|---|---|
| 4,211,239 A | * | 7/1980 | Raemer et al. | 600/529 |
| 4,619,269 A | * | 10/1986 | Cutler et al. | 600/532 |
| 4,965,560 A | * | 10/1990 | Riley | 345/1.1 |
| 5,394,521 A | * | 2/1995 | Henderson et al. | 715/804 |
| 5,687,717 A | * | 11/1997 | Halpern et al. | 600/300 |
| 5,758,110 A | * | 5/1998 | Boss et al. | 715/751 |
| 6,158,430 A | * | 12/2000 | Pfeiffer et al. | 128/202.27 |
| 6,834,647 B2 | * | 12/2004 | Blair et al. | 128/204.18 |

FOREIGN PATENT DOCUMENTS

| | | |
|---|---|---|
| DE | 27 50 450 C3 | 5/1979 |
| DE | 195 00 529 C2 | 8/1996 |

* cited by examiner

*Primary Examiner*—Justine R Yu
*Assistant Examiner*—Brian Won
(74) *Attorney, Agent, or Firm*—McGlew and Tuttle, P.C.

(57) ABSTRACT

A respiration system is provided, which has the greatest possible flexibility in operation based on a remote control (11), which is connected to a respirator (2) via separate data lines (9, 10) for display data and operating data. The display data are continuously displayed on both an operating unit (3) of the respiration system and the remote control (11). The operating data can only be entered either via the operating unit (3) of the respiration system or by the remote control (11).

12 Claims, 2 Drawing Sheets

RESPIRATION SYSTEM

CROSS REFERENCE TO RELATED APPLICATIONS

This application claims the benefit of priority under 35 U.S.C. § 119 of German Patent Application DE 10 2005 007 284.4 filed Feb. 17, 2005, the entire contents of which are incorporated herein by reference.

FIELD OF THE INVENTION

The present invention pertains to a respiration system (also known as a ventilator system) with an operating unit and with a respirator.

BACKGROUND OF THE INVENTION

A respiration system with an operating unit and with a respirator has become known from DE 195 00 529 C2. The prior-art respirator has an inspiration line and an expiration line in order to supply a patient with breathing gas and to remove expired gas. Fresh breathing gas is fed into the inspiration line via a breath flow regulating valve. For this, the breath flow regulating valve has preset values of a ramp generator for the breathing gas profile to be set. A control unit, which is connected to the breath flow regulating valve and a flow-measuring device for determining the breathing gas flow, contains in a memory suggested values for respiration parameters, which can be polled via the operating unit. The operating unit has for this purpose a display unit in the form of output sectors, via which variables that vary over time, such as the respiration pressure and the respiration gas flow or even selected forms of respiration are displayed. Settings of individual respiration parameters can be made by means of an input unit in the form of individual input sectors. The display unit and the input unit are imaged in terms of software on an interactive flat screen. A respiration parameter is activated by touching a corresponding segment on the flat screen.

A respirator, in which sensors arranged in pairs are provided for individual breathing gas parameters as a monitoring means in the inspiration line and in the expiration line, is known from DE 27 50 450 C3. The measured values of the individual sensors in the inspiration line are compared with those in the expiration line for calibration purposes in order to compensate drift effects. To adjust the sensors, the breathing gas flow can be deflected by means of individual valves such that the breathing gas being supplied by a gas mixer directly enters the sensor arrangement in the expiration line from the sensor arrangement in the inspiration line. A sensor defect can be inferred from a significant deviation between the measured values of sensors of the same type.

The drawback of the prior-art respirators is that operating and monitoring measures can be taken only directly at the device.

SUMMARY OF THE INVENTION

The basic object of the present invention is to propose a respiration system that has the greatest possible flexibility in operation.

Advantages of the present invention include that as an alternative to an operating unit arranged at the respirator, a remote control is connected to the respirator via separate data lines for transmitting display data and operating data. Corresponding to the operating unit, the remote control has for this a display field for outputting display data and an input field, via which respiration parameters can be entered or changed. The display data are transmitted via a first data line between the respirator and the display field of the remote control, and a second data line is provided for the exchange of the operating data between the operating field of the remote control and the respirator. A switchover device, which interrupts the exchange of operating data between the respirator and the input unit and establishes a data connection to the operating field of the remote control in a remote control mode, is provided in the second data line. Via a separate data channel, the display field of the remote control receives the information from the first data line, which information is transmitted from the respirator to the display unit of the operating unit. Thus, all display parameters are continuously present at both the operating unit of the respirator and the remote control. The flow of data can be changed by means of the switchover device such that changes in respiration parameters can be made only from the remote control. Manual control, with which the switchover between the local control mode can be performed from the operating unit to remote control mode via the remote control, is advantageously provided.

For sending an actuating signal for the switchover device in case a state of error is detected, the respirator is advantageously designed such that the local control mode is established by the actuating signal. The actuating signal is obtained here from a plausibility comparison of measured values of two sensors of the same type of a gas analyzer. The measured values of two oxygen sensors of the same type may be advantageously used for the plausibility comparison. The two oxygen sensors are preferably arranged in the inspiration line and they monitor the oxygen concentration there. If a significant deviation becomes established between the measured values of the oxygen sensors, this is interpreted by a control unit as a sensor defect and an actuating signal is generated for the switchover device. The respiration system is now again in the local control mode, and the user can perform the necessary settings directly from the operating unit looking at the patient.

An exemplary embodiment of the present invention is shown in the drawings and will be explained in greater detail below. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

Figure 1:
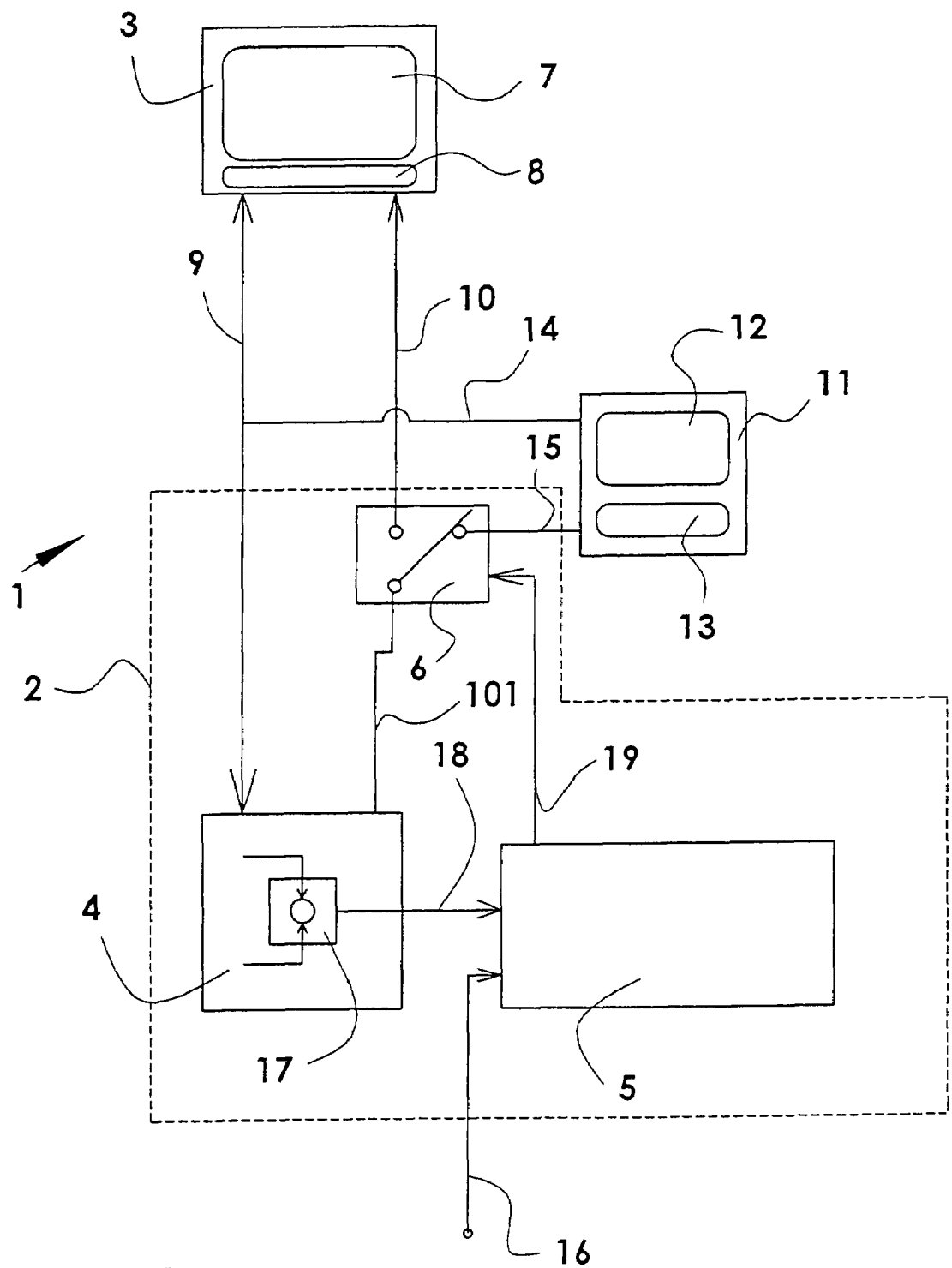
FIG. 1 is a schematic view showing the design of a respiration system according to the invention.

Referring to the drawings in particular, FIG. 1 schematically shows a respiration system 1 with a respirator 2 and an operating unit 3. The respirator 2 comprises a breathing gas supply unit 4, a control means 5 and a switchover device 6. The operating unit 3 contains a display unit 7 for displaying respiration curves and measured values as well as an input unit 8 for setting respiration parameters. A first data line 9 between the respirator 2 and the display unit 3 is used to transmit display data to the display unit. A second data line 10 connects the input unit 8 to the respirator 2. The switchover device 6, with which a remote control 11 can be connected to the respirator 2, is located in the second data line 10. Corresponding to the operating unit 3, a display field 12 and an input field 13 are provided at the remote control 11, the display field 12 being connected to the first data line 9 via a first data channel 14 and the input field 13 being connected to the switchover device 6 via a second data channel 15. Manual actuation of the switchover device 6 is possible by means of a manual control 16. A comparison unit 17 sends an electric actuating signal to the switchover device 6 via the control means 5 and lines 18, 19 if a state of error is present.

Figure 2:
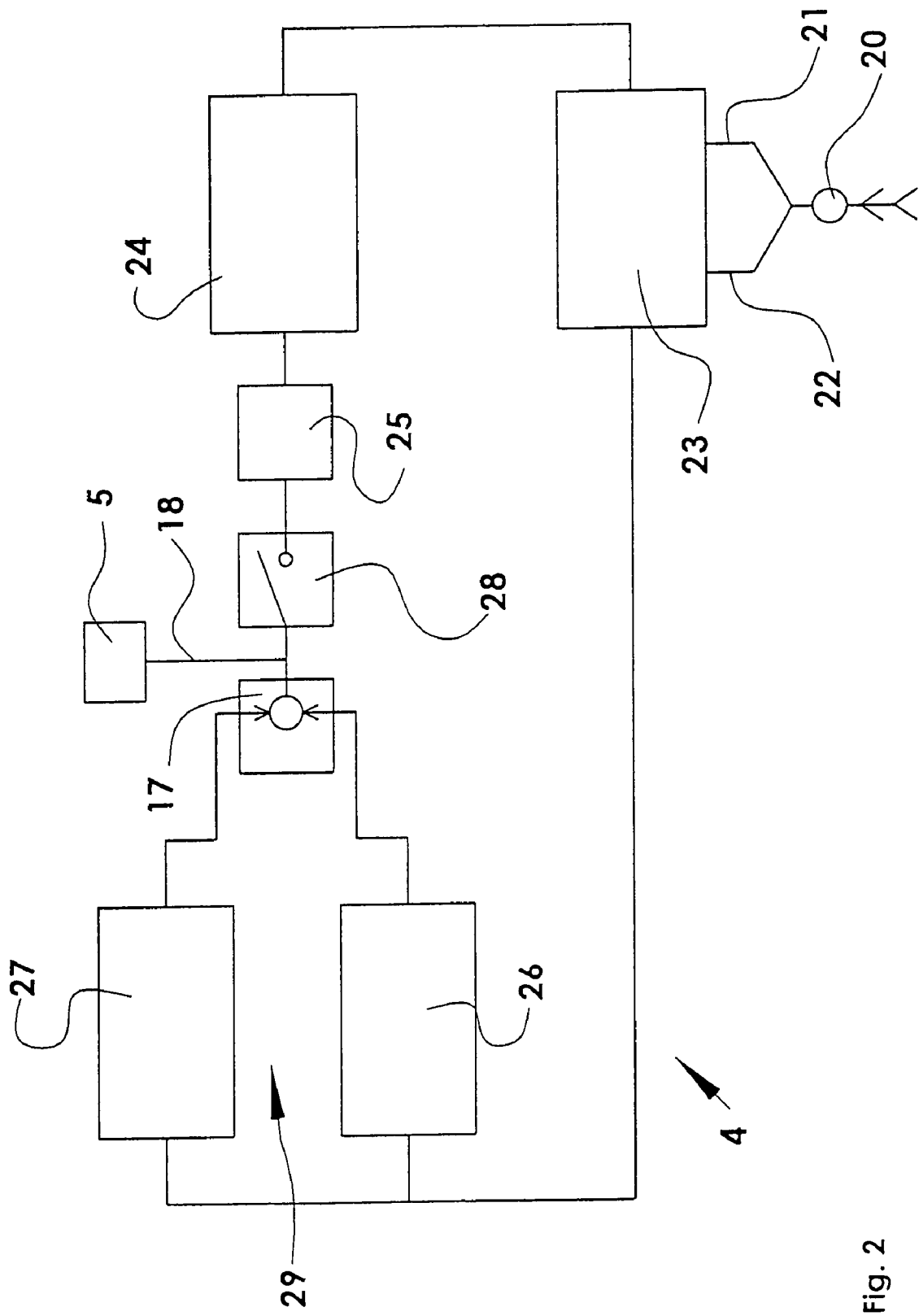
FIG. 2 is a schematic view showing the design of a breathing gas supply unit.

FIG. 2 schematically illustrates the design of the breathing gas supply unit 4. A patient 20 is connected to a breathing gas circuit 23 via an inspiration line 21 and an expiration line 22. A gas dispensing unit 24 with an actuating circuit 25 supplies the breathing gas circuit 23 with fresh breathing gas. The oxygen concentration in the breathing gas circuit 23 is measured with a first oxygen sensor 26 and a second oxygen sensor 27, which together form a gas monitor 29, and the preset values for the gas dispensing unit 24 are changed via the actuating circuit 25 until the desired oxygen concentration is present in the breathing gas circuit 23. This can be carried out in an automated manner by a control circuit, not shown in greater detail, which, shown schematically, is formed by closing a switch 28.

The oxygen sensors 26, 27 are arranged in the breathing gas circuit 23 such that they normally measure the same concentration. The comparison unit 17 will not detect any deviation between the measured values of the oxygen sensors 26, 27 during normal operation. In case of error, when the comparison unit 17 detects a significant deviation between the measured values of the oxygen sensors 26, 27, the switch 28 is opened and the dispensing of gas is switched over to manual operation. The detection of the state of error is sent to the control unit 5 via the line 18. The control unit 5 generates the actuating signal from this for the switchover device 6, FIG. 1.

The respiration system 1 according to the present invention operates as follows.

In the switching position of the switchover device 6 shown in FIG. 1 for a remote control mode, the input field 13 of the remote control 11 is connected to the respirator 2 via the line section 101 of the second data line 10. All current measured curves and individual values are displayed on the display field 12 of the remote control 11, and respiration parameters can be set via the input field 13. The current measured curves are likewise displayed on the display unit 7 on the operating unit 3 of the respirator 2, without respiration parameters being able to be changed. The switchover device 6 can be actuated via the manual control 16 of the respirator 2 such that a switchover from remote control mode via the remote control 11 is made to a local control mode via the operating unit 3.

The switchover from remote control mode to the local control mode is also initiated when a significant deviation of the measured values of the oxygen sensors 26, 27 is detected at the comparison unit 17 of the breathing gas supply unit 4. A corresponding data protocol is now sent to the control unit 5 via the line 18, and an actuating signal, with which the switchover device 6 is switched over to the local control mode via the line 19, is generated there at the control unit 5. Changes can then be made in the respiration parameters via the input unit 8 of the operating unit.

While a specific embodiment of the invention has been shown and described in detail to illustrate the application of the principles of the invention, it will be understood that the invention may be embodied otherwise without departing from such principles.

What is claimed is:

1. A respiration system comprising:
   an operating unit comprising a display unit and an input unit for respiration parameters;
   a respirator comprising a breathing gas line for supplying a patient with breathing gas, a fresh gas supply unit and a gas monitor for the analysis of at least one parameter of the breathing gas, said operating unit being arranged at said respirator;
   a first data line between said respirator and said display unit for transmitting display data;
   a second data line between said respirator and said input unit for transmitting settings of respiration parameters;
   a remote control comprising a display field and an input field;
   a first data channel between said first data line and said display field;
   a second data channel connected to said input field; and
   a switchover device connected to said second data line and to said second data channel, said switchover device changing from a local control mode to a remote control mode, with the change interrupting the exchange of data between said respirator and said input unit via said operating unit, to prevent settings of respiration parameters from being input to said respirator via said operating unit, and establishing a data connection between said respirator and said input field of said remote control via said second data channel, to only allow settings of respiration parameters to be input to said respirator via said remote control input field.

2. A respiration system in accordance with claim 1, further comprising a manual control for switching over between the remote control mode and the local control mode.

3. A respiration system in accordance with claim 1, wherein said respirator is designed to send an actuating signal for said switchover device in case a state of error is detected such that the local control mode is established by the actuating signal.

4. A respiration system in accordance with claim 3, wherein said actuating signal is generated from a plausibility comparison of measured values of two sensors of the same type.

5. A respiration system comprising:
   an operating unit having a display unit and an input unit for input of respiration parameters;
   a respirator with a breathing gas circuit with line for supplying a patient with breathing gas, a breathing gas fresh gas dispensing unit supplying breathing gas to said breathing gas circuit and a gas monitor for the analysis of at least one parameter of the breathing gas, said operating unit being arranged at said respirator;
   a first data line providing data communication between said respirator and said display unit for transmitting display data;
   a second data line providing data communication between said respirator and said input unit for transmitting operating data including settings of respiration parameters;
   a remote control comprising a display field and an input field;
   a first data channel providing data communication between said first data line and said display field;
   a second data channel connected to said input field; and
   a switchover device connected to said second data line and connected to said second data channel for changing between a local control mode and a remote control mode, with said local control mode providing a data connection between said respirator and said input unit via said operating unit and said second data line for transmitting operating data including settings of respiration parameters and said remote control mode providing a data connection between said respirator and said input field of said remote control via said second data channel and part of said second data line, with said first data line still providing data communication between said respirator and said display unit for transmitting display data and with said display field and said first data channel providing data communication between said first data line and said display field, wherein a change from said local control mode to said remote control mode includes an interruption of the exchange of data between said respirator and said input unit via said operating unit on said second data line, to prevent operating data including settings of respiration parameters from being input to said respirator via said operating unit, and an establishing of a data connection between said respirator and said input field of said remote control via said second data channel and part of said second data line, to only allow operating data including settings of respiration parameters to be input to said respirator via said remote control input field, and a change from said remote control mode to said local control mode includes an interruption of the exchange of data between said respirator and said input field of said remote control via said second data channel and part of said second data line, to prevent operating data including settings of respiration parameters from being input to said respirator via said remote control input field, and establishing the data connection between said respirator and said input unit via said operating unit and said second data line, to only allow operating data including settings of respiration parameters to be input to said respirator via said operating unit.

6. A respiration system in accordance with claim 5, further comprising a manual control for switching over between the remote control mode and the local control mode.

7. A respiration system in accordance with claim 5, wherein said respirator sends an actuating signal for said switchover device in case a state of error is detected such that the local control mode is established by the actuating signal.

8. A respiration system in accordance with claim 7, wherein said actuating signal is generated from a plausibility comparison of measured values of two sensors of the same type.

9. A method of operating a respiration system, the method comprising the steps of:
providing an operating unit having a display unit and an input unit for input of settings of respiration parameters;
providing a respirator with a breathing gas circuit with a breathing gas line for supplying a patient with breathing gas, a breathing gas fresh gas dispensing unit supplying breathing gas to the breathing gas line and a gas monitor for the analysis of at least one parameter of the breathing gas, said operating unit being arranged at said respirator;
establishing a first data line providing data communication between the respirator and the display unit for transmitting display data;
providing a remote control comprising a display field and an input field;
establishing a first data channel providing data communication between the first data line and the display field;
providing a local control mode with a data connection between the respirator and the input unit via the operating unit and a second data line for transmitting operating data including settings of respiration parameters between the respirator and the operating unit;
providing a remote control mode with a data connection between the respirator and the input field of the remote control via the second data channel and part of the second data line;
switching between the local control mode and the remote control mode wherein a change from the local control mode to the remote control mode includes an interruption of the exchange of data between the respirator and the input unit via the operating unit on the second data line, to prevent operating data including settings of respiration parameters from being input to said respirator via said operating unit, and establishing a data connection between the respirator and the input field of the remote control via the second data channel and part of the second data line, to only allow operating data including settings of respiration parameters to be input to said respirator via said remote control input field, and a change from the remote control mode to the local control mode includes an interruption of the exchange of data between the respirator and the input field of the remote control via the second data channel and part of the second data line, to prevent operating data including settings of respiration parameters from being input to said respirator via said remote control input field, and establishing the data connection between the respirator and the input unit via the operating unit and the second data line, to only allow operating data including settings of respiration parameters to be input to said respirator via said operating unit.

10. A method in accordance with claim 9, further comprising providing a manual control for switching over between the remote control mode and the local control mode.

11. A method in accordance with claim 9, wherein the respirator sends an actuating signal for the switchover device in case a state of error is detected such that the local control mode is established by the actuating signal.

12. A method in accordance with claim 11, wherein the actuating signal is generated from a plausibility comparison of measured values of two sensors of the same type.

* * * * *